(12) United States Patent
Moser

(10) Patent No.: US 6,642,214 B1
(45) Date of Patent: Nov. 4, 2003

(54) DETOXICATION OF ACTIVE PHARMACEUTICAL SUBSTANCES USING CYCLODEXTRINE OLIGOMERS

(75) Inventor: Joerg G Moser, Duesseldorf (DE)

(73) Assignee: CeramOptec Industries, Inc., East Longmeadow, MA (US)

( * ) Notice: Subject to any disclaimer, the term of this patent is extended or adjusted under 35 U.S.C. 154(b) by 0 days.

(21) Appl. No.: 09/554,223

(22) PCT Filed: Nov. 11, 1998

(86) PCT No.: PCT/EP98/07229

§ 371 (c)(1),
(2), (4) Date: Aug. 3, 2000

(87) PCT Pub. No.: WO99/24474

PCT Pub. Date: May 20, 1999

(30) Foreign Application Priority Data

Nov. 11, 1997 (DE) .......................................... 197 49 801
May 19, 1998 (DE) .......................................... 198 22 416

(51) Int. Cl.⁷ ........................ A61K 31/715; C08B 37/16
(52) U.S. Cl. ........................................ 514/58; 536/103
(58) Field of Search ............................. 536/103; 514/58

(56) References Cited

U.S. PATENT DOCUMENTS 5,474,765 A * 12/1995 Thorpe ................... 424/178.17
5,762,918 A *  6/1998 Thorpe .................... 424/78.01

FOREIGN PATENT DOCUMENTS

WO        WO9113100         9/1991
WO        WO 99/24474 A1 *  5/1999

OTHER PUBLICATIONS

Antlsperger et al., "Toxicological Comparison of Cyclodextrins," published in *Proceedings of the Eighth International Symposium on Cyclodextrin*, Budapest, Hungary, Mar. 31–Apr. 2, 1996, Kluwer Academic Publishers, Netherlands, 1996, only pp. 149–155 supplied.*

Bosslet, "Aspekte der Zielgerichteten Tumortherapie," *Die Gelben Hefte, 32*, 149–155 (1992).*

Bodanszky et al.(eds.), *The Practice of Peptide Synthesis*, Springer–Verlag, New York, NY, 1984, only title pages supplied.*

Fujita et al., "6A6B, 6A6C , and 6A6D–Ditosylates of β–Cyclodextrins," *Tetrahedron Letters*, 25(48), 5533–5536 (1984).*

Fazio et al., Antibody–Guided Scintigraphy: Targeting of the "Magic Bullet," *European Journal of Nuclear Medicine*, 20(12), 1138–1140 (Dec., 1993).*

Breslow et al., "Molecular Recognition by Cyclodextrins," *Tetrahedron*, 51(2), 377–388 (Jan. 9, 1995).*

Sharma et al., "Pharmaceutical and Physical Properties of Paclitaxel (Taxol) Complexes with Cyclodextrins," *Journal of Pharmaceutical Sciences*, 84(10), 1223–1230 (Oct., 1995).*

Feederle et al., "Metabolism of Cyclodextrins by *Klebsiella oxytoca* M5a1: Purification and Characterization of a Cytoplasmically Located Cyclodextrinase," *Archives of Microbiology*, 165, 206–212 (1996).*

Savitsky et al., "Avidin–Biotin System for Targeting Delivery of Photsensitizers and Other Cytotoxic Agents into Malignant Tissue," presented at the conference titled *Photochemotherapy: Photodynamic Therapy and Other Modalities*, K. Berg (ed.), San Remo, Italy, Sep., 1997, published in *Proceedings–SPIE The International Society for Optical Engineering*, 3191, 343–354 (1997).*

A. Ruebner et al., "Dimeric Cyclodextrin Carriers with High Binding Affinity to Porphyrinoid Photosensitizers", Journal of Inclusion Phenomena and Molecular Recognition in Chemistry, Bd. 27, 1997, pp. 69–84.

J.G. Moser et al., "Cyclodextrin Dimers Used to Prevent Side Effects of Photochemotherapy and General Tumor Therapy", Journal of Inclusion Phenomena and Molecular Recognition in Chemistry, Bd. 25, 1996, pp. 29–34.

T. Cserhati and J. Hollo, "Interaction of Taxol and other Anticancer Drugs with Hydroxypropyl–beta–cyclodextrin", International Journal of Pharmaceutics, Bd. 108, 1994, pp. 69–75.

* cited by examiner

Primary Examiner—James O. Wilson
Assistant Examiner—Lawrence E Crane
(74) *Attorney, Agent, or Firm*—BJ Associates; Bolesh J. Skutnik

(57) ABSTRACT

A cyclodextrin oligomer comprising two cyclodextrins connected through a spacer at the secondary side, characterized in that said spacer comprises the unit B which is a rigid and preferably hydrophilic structural element.

12 Claims, 6 Drawing Sheets

(example 3C)

Dimer for the encapsulation of taxol spacing of cyclodextrins  
―――――――――――――  
1.55 nm spacing of biotins: 2.46 nm

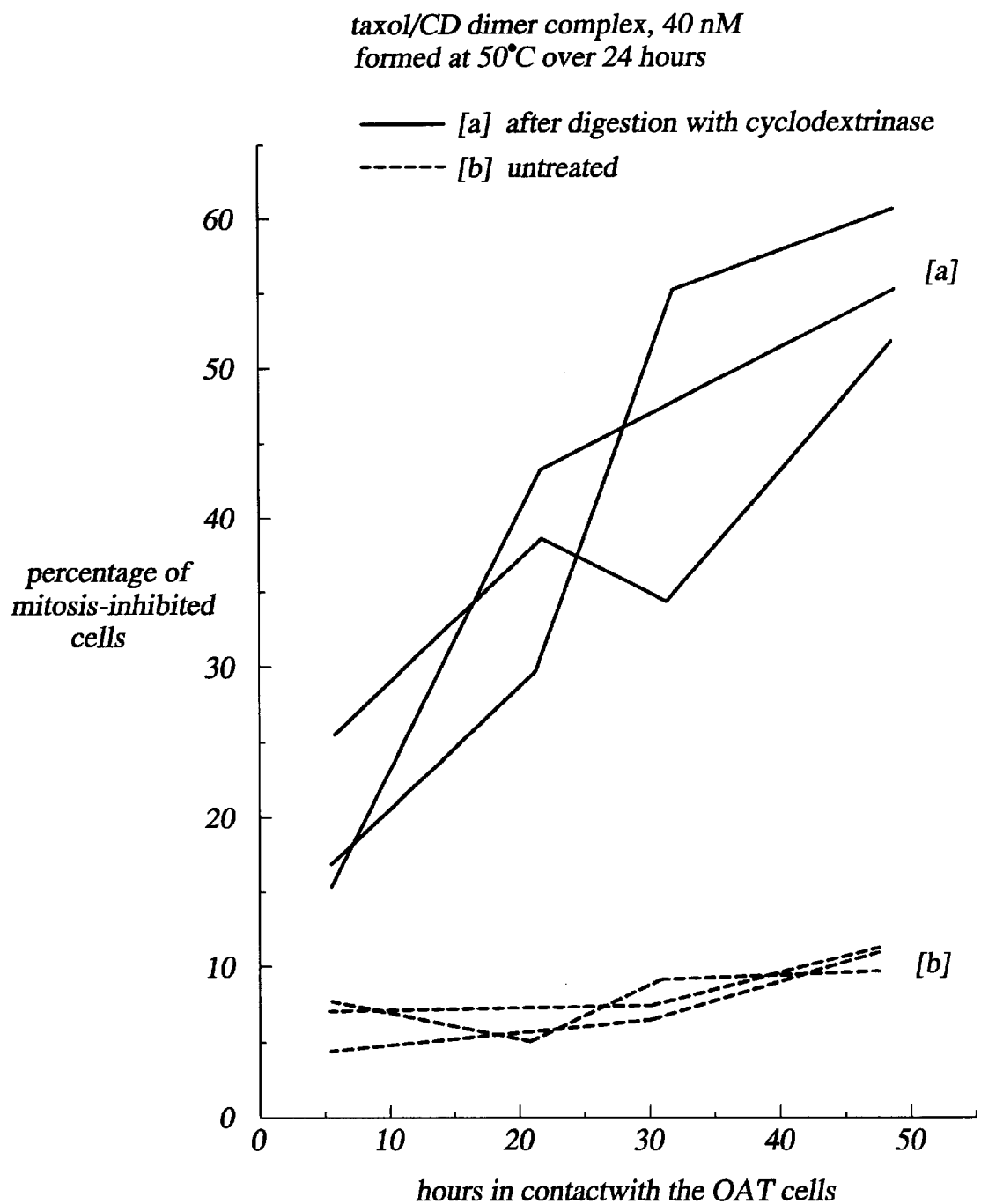
FIG.5 (EXAMPLE 8):

FIG.6  *Most probable structure of the paclitaxel/CD dimer complex*
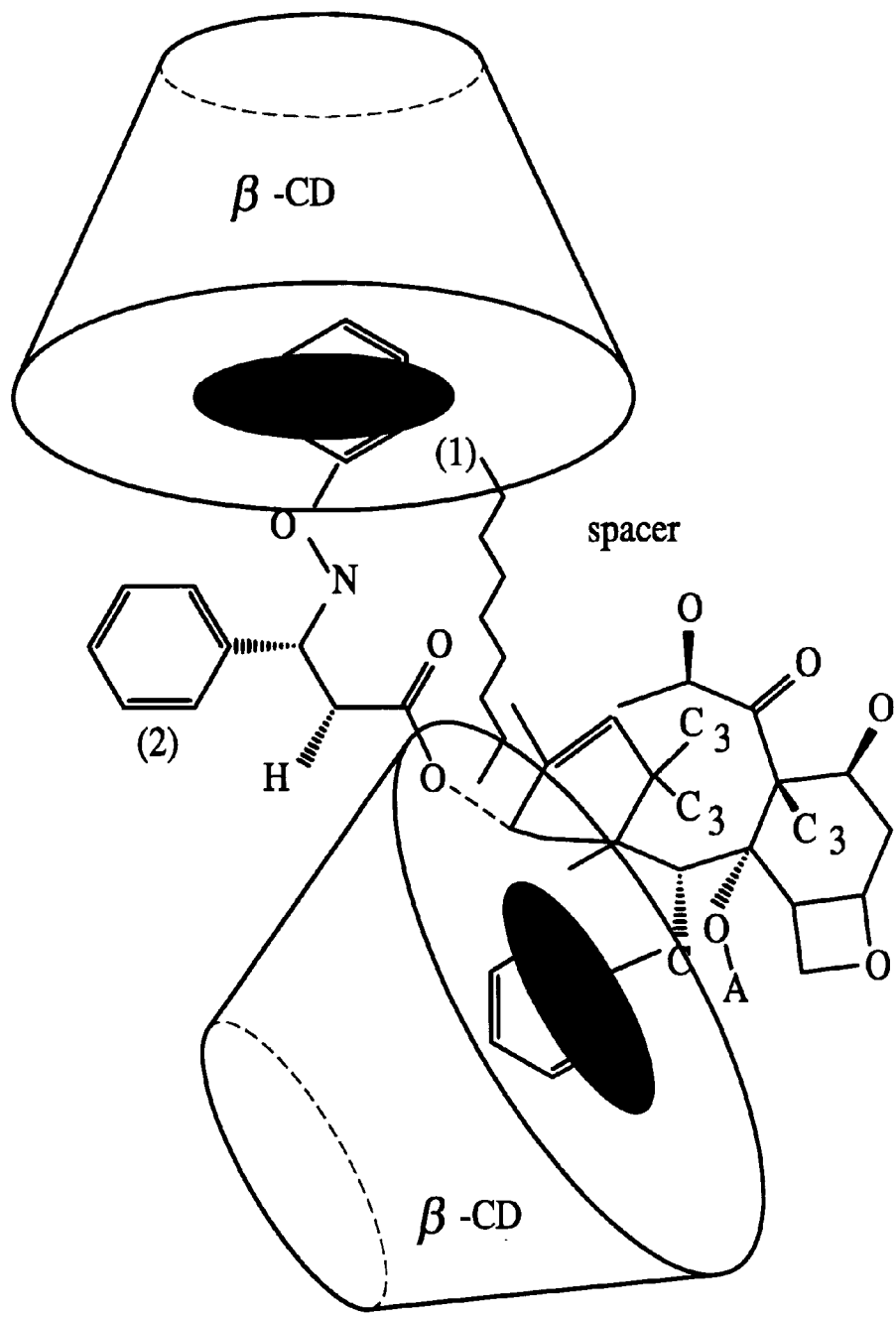

DETOXICATION OF ACTIVE PHARMACEUTICAL SUBSTANCES USING CYCLODEXTRINE OLIGOMERS

The present invention relates to spacer-bridged cyclodextrin oligomers, and to complexes of such cyclodextrin oligomers with pharmaceutically active substances.

Cyclodextrins are circular glucose polymers which are referred to as α-, β- or γ-cyclodextrins, depending on the number of glucose units (6 to 8, respectively). A lipophilic cavity exists inside the oligoglucose ring. It is known that lipophilic substances can be enclosed within this cavity. Cyclodextrins are used, inter alia, for converting compounds having low solubility to a soluble complex by complex formation with cyclodextrin.

In Tetrahedron, Vol. 51, 2 (1995), p. 377–388, R. Breslow et al. describe cyclodextrin dimers which are capable of binding substrates having the correct geometry in aqueous solutions.

In the Journal of Inclusion Phenomena and Molecular Recognition in Chemistry, 27 (1997), p. 69–84, A. Ruebner et al. describe dimeric cyclodextrins having high binding affinities for porphyrinoid photosensitizers as a carrier system for the application of drugs in photodynamical cancer therapy.

In Tetrahedron Letters 25 (1984), p. 5533–5536, K. Fujita et al. describe the preparation of ditosylates of β-cyclodextrin and their purification by reversed-phase chromatography.

In Tetrahedron Letters 18 (1977), p. 1527–1530, I. Tabushi et al. describe the specific bifunctionalization of cyclodextrin.

In Arch. Microbiol. 165 (1996), p. 206–212, R. Feederle et al. describe the purification and characterization of the enzyme cyclodextrinase from *Klebsiella oxytoca*.

In an electronic publication which is accessible under http://antas.agraria. uniss.it/electronic_papers/eccc3/bcd/welcome.htm, B. Manunza et al. describe a molecular dynamics study of the structure and internal movement of solvated β-cyclodextrin.

In the Journal of Pharmaceutical Sciences 84 (1995), p. 1223–1230, U. S. Sharma et al. describe the pharmaceutical and physical properties of paclitaxel (taxol) complexes with cyclodextrins.

In SPIE Biomedical Optics 3191 (1997), p. 343–353, A. P. Savitsky et al. describe an avidin-biotin system for the selected transport of photosensitizers and other cytotoxic agents into tumor tissue.

In Eur. J. Nucl. Med. 20 (1993), p. 1138–1140, F. Fazio & G. Paganelli describe that such biotin-avidin systems enable a highly specific labeling of tumors.

It has been the object of the present invention to provide cyclodextrin oligomers which are suitable for the inclusion of pharmaceutically active substances due to their geometry.

The cyclodextrin oligomers according to the invention are two cyclodextrins connected through a spacer at the secondary side, the spacer comprising the unit B which is a rigid and preferably hydrophilic structural element. In one embodiment, the cyclodextrin oligomers have the general formula

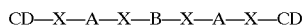

where each X is independently selected from —NH—, —O—, —S—, —CO— or a covalent bond;

each A is an aliphatic $C_2$ to $C_4$ residue or a covalent bond;

B is a rigid and preferably hydrophilic structural element; and each CD represents a cyclodextrin bound through its secondary side.

Preferred compounds for the unit B include melamine, trimesic acid, alizarintetracarboxylic acid or tetraaminoalizarin, and cyclodextrins, such as α-cyclodextrin, β-cyclodextrin or γ-cyclodextrin, the cyclodextrins being preferably bound through their primary sides.

As examples of the cyclodextrin oligomers according to the invention, there may be mentioned the compounds:

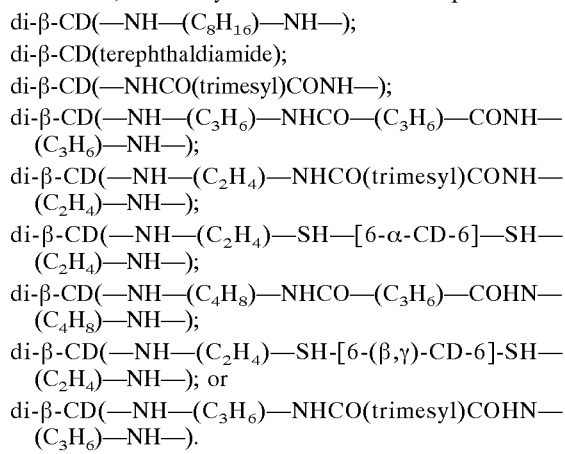

The cyclodextrin oligomers according to the invention can be obtained by the tosylation of the OH groups on the secondary side of cyclodextrins, followed by reaction with short bifunctional spacer groups. The thus obtained functionalized cyclodextrins can be converted to dimers with bifunctional reagents. The corresponding synthetic protocols can be found in A. Ruebner et al. (loc. cit.). Alternatively, carboxylic acid functions may also be introduced into the cyclodextrins by reacting the regiospecific tosylates with amino- or mercaptocarboxylic acids, such as 3-mercaptopropionic acid or 4-aminobutyric acid.

Binding constants can be determined in competition with 6-(p-toluidino)-2-naphthalenesulfonic acid (TNS). The measurement is performed by fluorescence spectroscopy according to Ruebner et al. (loc. cit.).

Preferably, the cyclodextrin oligomer additionally carries at least one and preferably two affinity groups which can interact with molecular target structures.

In principle, said at least one affinity group can have binding capability for a tissue-specific antigen as a molecular target structure. However, according to the polyphasic application route sought by Fazio & Paganelli (loc. cit.), an indirect tissue-specific binding is preferred: The affinity group recognizes a target structure which was previously attached at the desired site of action in a tissue-specific way.

For example, a possible site of action is a tumor. Thus, a tissue- or tumor-specific antibody which carries the target structure for the affinity group of the substance according to the invention can first be introduced into the organism once or several times to become enriched at the site of action, in terms of a polyphasic tumor therapy. Subsequently, a selective enrichment of the pharmaceutically active substance can be achieved at the site of action by the administration of a complex of a pharmaceutically active substance and the substance according to the invention having the affinity group. Then, the pharmaceutically active substance can be released at the site of action. This is effected, for example, by disrupting the cyclodextrin unit(s) at the site of action. Poly- or monoclonal antibodies, but also antibody fragments, such as Fab or F(ab)$_2$ fragments, and artificial antibodies such as scFv fragments, can be used as said antibodies. Suitable affinity groups and target structures include a wide variety of binding members, such as biotin/avidin, biotin/streptavidin or enzyme/inhibitor systems. Preferred affinity groups include biotinyl residues and digoxin/digoxigenin residues.

Therefore, the invention further relates to a complex of a pharmaceutically active substance and the cyclodextrin oligomers according to the invention. These physical inclusion complexes, which are highly hydrophilic externally, serve to prevent the uptake of the complexed pharmaceutically active substance into body cells for the purpose of reducing or excluding the side-effects of tumor therapeutics, for example. Preferably, the pharmaceutically active substance has a high potential for side-effects and can therefore be employed in its free form only in a limited way. Suitable pharmaceutically active substances include mitotic inhibitors, tumor therapeutics and photo-chemotherapeutics, especially taxol, a taxol derivative, coichicine, colchemide, $3^1,8^1$-(di-t-butylphenoxy)porphyrin, chlorotrianisene, tamoxifene, vinblastin, vincristin, docetaxel.

If the cyclodextrin oligomers carry an additional affinity group, they can serve for the selective polyphasic application of a pharmaceutically active substance. Surprisingly, the hepatocellular carcinomas, pulmonary carcinomas, lymphomas, melanomas, ovarial carcinomas and prostatic carcinomas.

In a preferred embodiment, the cyclodextrin oligomer is di-β-CD(—NH—(C$_4$H$_8$)—NHCO—(C$_3$H$_6$)—CONH—(C$_4$H$_8$)—NH—), and the pharmaceutically active substance is taxol or a taxol derivative.

The indication, dosage and successes of treatment in tumor diseases are described in: Proceedings ASCO, Vol. 16 (1997) (Denver, Colo., USA).

Due to the cyclodextrins being bonded on the secondary side, the cavities of the cyclodextrins are oriented towards each other. The cyclodextrins are preferably β-cyclodextrins. The distance between the cyclodextrin units is determined by selecting the spacer. Depending on the size of the compound to be enclosed, the spacer is selected such that the distance between the at least two cavities approximately matches the distance between two hydro-phobic groups of the pharmaceutically active substance. Preferred spacings are within a range of about 0.6 to 2 nm, more preferably in a range of about 0.8, 1.0, 1.2, 1.4, 1.6 and 1.8 nm. Such compounds are shown in the following Table.

Inclusion of various homo- and heteroditopical pharmaceuticals into "tailor-made" dimeric or trimeric β-cyclodextrin oligomers: Structure and spacing length of the spacers

| Length of the spacer Δ ⇔ [Å] | Spacer structure for dimers | Spacer structure for trimers | Affinity constant, measured/estimated [l/mol] | possible guest compounds |
|---|---|---|---|---|
| For spacer Δ ≤ 6 Å, see ref. Breslow et al. (1995) | | | | |
| 7–8 | octyl-α,ω-diamide = (—NH—(C$_8$H$_{16}$)—NH—) | ./. | $10^6$–$10^7$ | $3^1,8^1$-(di-t-butylphenoxy)-porphyrinoids for PDT****, (tamoxifene), phenytoin as standard substance |
| 9–10 | —NHCO(trimesyl-X**-biotinyl)CONH— | ./. | $10^6$–$10^7$ | chlorotrianisene, tamoxifene |
| 11–12 | A3C5A3*** = —NH—(C$_3$H$_6$)—NHCO—(C$_3$H$_6$)—CONH—(C$_3$H$_6$)—NH— | ./. | $10^6$–$10^7$ | colchicine*, colchemide* |
| 13–14 | —NH—(C$_2$H$_4$)—NHCO(trimesyl-X**-biotinyl)-CONH—(C$_2$H$_4$)—NH— | —NH—(C$_2$H$_4$)—SH—[6-α-CD-6]—SH—(C$_2$H$_4$)—NH— | ~$10^8$ | vinblastin*, vincristin* |
| 15–16 | A4C5A4*** = —NH—(C$_4$H$_8$)—NHCO—(C$_3$H$_6$)—CONH—(C$_4$H$_8$)—NH— or- NH—(C$_3$H$_6$)—NHCO(trimesyl-X**-biotinyl)-CONH—(C$_3$H$_6$)—NH— or alizarin derivative as shown in FIG. 2 | —NH—(C$_2$H$_4$)—SH—[6-(β,γ)-CD-6]—SH—(C$_2$H$_4$)—NH— as in FIG. 1 | $10^7$ (dimer)– $3 \cdot 10^9$ (trimer) | paclitaxel, docetaxel |

Remarks:
*hetero-ditopical;
**trimesyl-X- = tricarboxybenzoylmonocadaveryl-;
***nomenclature according to Ruebner et al. (1998);
****PDT = photodynamical tumor therapy side-effects of a therapy can be reduced by this method. In addition, a considerable dosage reduction of up to a factor of 10,000 is possible.

The invention also relates to medicaments which contain at least one cyclodextrin oligomer according to the invention or at least one complex according to the invention. Such medicaments are useful, in particular, for the treatment of tumor diseases, such as tumors of the bladder, carcinomas of the breast or uterus, esophageal cancers, gastric carcinomas, cephalo-cervical carcinomas, nasopharynx carcinoma, The spacer between the two cyclodextrin units is rigid, i.e., the spacer has only a small number of bonds which can freely rotate about the binding axis. Preferably, the spacer contains an additional cyclodextrin unit which is preferably bound to the complexing cyclodextrins through its primary side and through short aliphatic spacers.

Such rigid spacers can also be achieved by the use of appropriately functionalized (hetero)aromatics. For example, rigid spacers prevent too high a conformational flexibility, such as twisting of the two cyclodextrins involved in the binding. This results in comparably high binding constants as stated in the above Table. By the use of rigid spacers, affinity constants within a range of greater than $10^6$, preferably greater than $10^7$ and more preferably greater than $10^8$ l/mol are achieved. Thus, rigid spacers are those which achieve correspondingly high stability constants of the complexes together with cyclodextrins involved in the binding and appropriate guest compounds.

The complexes according to the invention can be disrupted, for example, by the action of cyclodextrinase from Klebsiella oxytoca to release the complexed pharmaceutically active substance. Alternatively, functional groups can be contained in the spacers which facilitate the breaking of the bond at the target site.

FIG. 5 shows the reactivation of taxol from the complex by treatment with cyclodextrinase according to Example 8.

FIG. 6 shows the most probable structure of the paclitaxel/cyclodextrin dimer complex.

Figure 1:
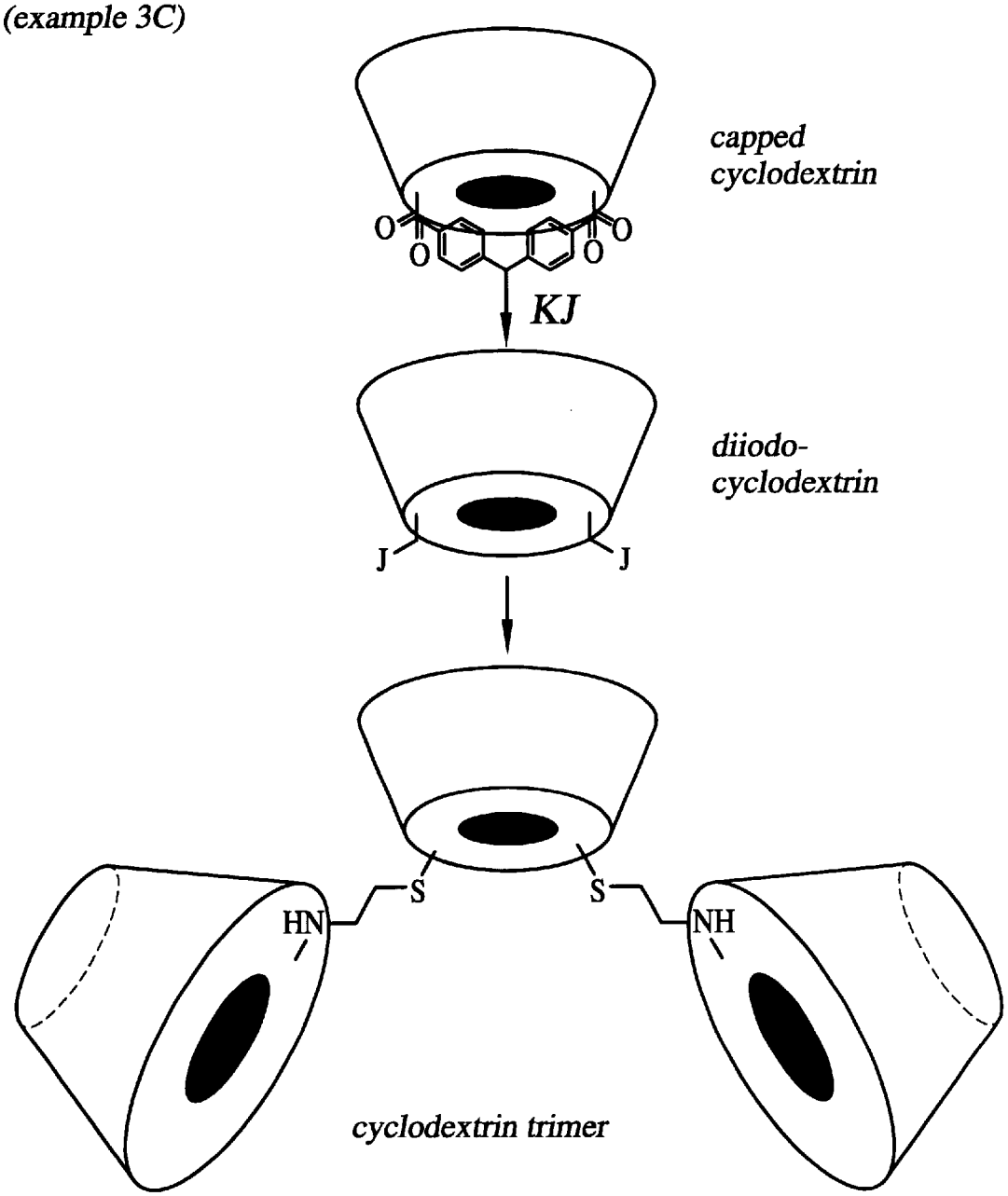
FIG. 1 shows a scheme for the synthesis of a trimeric cyclodextrin.

The following Examples are intended to further illustrate the method according to the invention.

EXAMPLE 1

Synthesis of a β-[1,6(A-D)]-capped Cyclodextrin and Its Further Conversion to β(6)-diamidopropyldiaminocyclodextrin 3 g of β-cyclodextrin (Wacker Chemie, Burghausen) which had been dried in an oven at 105° C. was dissolved in 50 ml of pyridine. A solution of 1 g of 4,4-methylenebis (benzenesulfonic acid)dichloride in 50 ml of pyridine was slowly added dropwise. The mixture was stirred at room temperature for 3 hours. Then, 10 ml of water was added, and all solvents were removed in a rotary evaporator at 70° C. The remaining sirup was treated twice with water and evaporated, followed by dissolving in 10 ml of water and precipitation in 500 ml of acetone. MALDI mass spectroscopy showed a molecular weight of $(M+Na^+)=1451(1)$.

Substance (1) can be further purified by reversed-phase chromatography.

The substance was further treated with a tenfold excess of diaminopropane to obtain β-[6(A-D)] diamidopropanediaminocyclodextrin (2). Thus, a solution of substance (1) in hot water was added dropwise to an aqueous solution of diaminopropane and stirred at 70° C. for 3 hours. The product concentrated by evaporation was precipitated in acetone-methanol 20:1 and further purified by Soxhlet extraction with acetone-methanol (4:1).

Further purification is achieved by ion-exchange chromatography on SP Sephadex with a gradient of water to 2 M triethylamine in water.

Similarly, α- and γ-cyclodextrin can be reacted with the reagent and further processed in the way described.

EXAMPLE 2

β-(2S)-monotosylcyclodextrin and Its Conversion to β-(2)-cyclodextrin(3-thiopropionic Acid) or β-(2S)-cyclodextrin(3-thiopyruvic Acid) or β-(2S) -cyclodextrin(2-thioacetic Acid)

2.5 g of 2-monotosyl-β-cyclodextrin prepared and purified according to Ruebner et al. (1997) was dissolved in 40 ml of dimethylformamide (DMF). Further, 1.7 g of 3-mercaptopropionic acid was dissolved in 60 ml of DMF, and 0.3 g of dry $K_2CO_3$ was added. This solution was heated at 70° C., and the first solution was added dropwise thereto. After three hours of stirring, the solution was cooled, filtered and evaporated in a rotary evaporator. The sirupy residue was precipitated in acetone, and the precipitate was dried. Further chromatographic purification was effected on QAE Sephadex with elution by a gradient of 0 to 2 M formic acid. MALDI: $(M+K^+)=1263$.

β-(2S)-cyclodextrin(3-thiopyruvic acid) (under an argon atmosphere) and β-(2S)-cyclodextrin(2-thioacetic acid) can be prepared in a similar way.

EXAMPLE 3

Formation of Trimers from the Substances of Examples 1 and 2

Several methods for the preparation of cyclodextrin trimers were successfully tried with the substances of Examples 1 and 2.

(A) The product from Example 2 was dissolved in a small volume of DMF, a 20 fold molar excess of carbonyidiimidazole was added, and the solution was heated at 70° C. for 30 min. A small amount of N-hydroxysuccinic amide was added. Then, a two-and-a-half-fold molar excess of the substance from Example 1 was added, and the solution was stirred for 2 hours. The product was concentrated in vacuo and precipitated with acetone. Further purification by sequential ion-exchange chromatography on SP and QAE Sephadex yielded the pure trimer.

(B) The product from Example 2 was dissolved in a small volume of aqueous phosphate buffer (pH 5.5), and a 20 fold molar excess of EDAC and a small amount of N-hydroxysuccinic imide were added. After 30 min, a 2.5 fold molar excess of the substance from Example 1 in an aqueous solution was added dropwise. The reaction mixture was allowed to stand in a cool room at 4° C. for 4 days with stirring. Further purification was performed as described under (A).

(C) Purified capped cyclodextrins could be directly reacted with cysteamine in DMF to give dicysteaminylcyclodextrins. The products were precipitated in acetone and further reacted with 2-tosyl-β-cyclodextrin at 70° C. in DMF. These short-chained trimers could be further purified by reversed-phase chromatography on Lichroprep RP8.

EXAMPLE 4

Formation of Physical Inclusion Complexes Between a Pharmaceutically Active Substance and Trimeric Cyclodextrins According to Example 3. General Method and Purification of the Complexes The pharmaceutically active substances were dissolved in ethanol or dimethyl sulfoxide for complexation and added to a substance according to Example 3 in water or phosphate-buffered physiological saline (PBS). The solutions were heated at 70° C. in a rotary evaporator and briefly evacuated to remove the ethanol. After cooling, the solutions were charged on a column with TSK gel and eluted with water or PBS. The first fractions (which may be colored) contain the pure complex.

EXAMPLE 5

Biological Testing with Complexes According to Example 4. Injections and Infusions in Test Animals Purified complexes according to Example 4 were injected intravenously into mice or rats in doses of from 2 to 5 mg/kg in accordance with the quantitative assay by fluorescence or absorption spectrometry. The urine and faeces of the animals were collected. After 24 hours, the animals were sacrificed, and their organs processed for fluorescence analysis. This is preferably effected by extraction with methanol:acetone 1:1 since the complexes according to the invention can be dissociated using these solvents. Less effective is the dissolution of organ homogenizates in 2% sodium dodecylsulfate in aqueous solution, followed by fluorescence spectroscopy. In this way, the quantity of the bound guest molecule in different organs can be determined, and thus, conclusions as to the pharmacokinetics of the complexes can be drawn.

EXAMPLE 6

Encapsulation of Taxol into the CD Dimer 250 mg (100 μmol) of the CD dimer di-β-CD(2N-A4C5A4) (see FIG. 5) was dissolved in 1 l of aqueous buffer (pH 7.35, Hepes 25 mM) at 60° C. and kept at this temperature with vigorous stirring. 8.5 mg of paclitaxel (10 μmol) was dissolved in 1 ml of dimethyl sulfoxide and added dropwise to the mixture with vigorous stirring. The mixture was kept at 60° C. for 24 hours with stirring, followed by cooling and freeze-drying the mixture. The fluorescence spectrum (FIG. 1) shows the monomerization of the complexed taxol.

In a competitive reaction with toluidinonaphthalene-sulfonic acid, a complex binding constant $K_{taxol}$=1.4 μM is found. Complex formation can be performed similarly with CD dimers to which biotin is attached through a C5 spacer (cadaverine). The binding capability of biotin to avidin is not affected by such treatment at 60° C.

EXAMPLE 7

Purification of the Complex by Gel Chromatography on TSK Gel

The mixture was dissolved in 10 ml of water and charged onto a chromatographic column (3×100 cm) filled with TSK gel. Upon fractionated elution with water, the 1st peak contains the pure complex purified from accompanying materials. Detection was effected in a flow mode at 260 or 280 nm. The product was sterilized from the eluate by filtration through a sterile filter with 0.2 μm pore size.

EXAMPLE 8

Testing of the Complex for Toxicity in a Cell Culture

Figure 2:
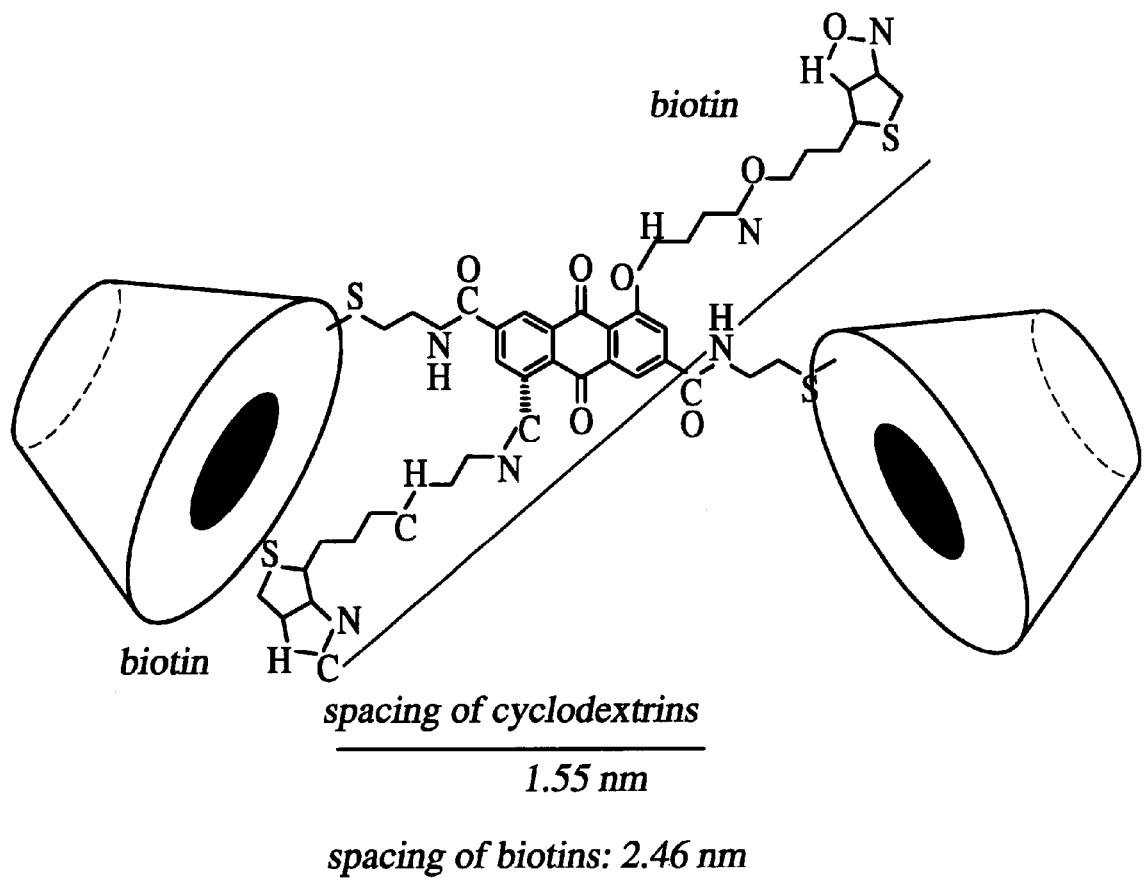
FIG. 2 shows the structure of alizarin-bridged cyclodextrins derivatized with two biotinyl affinity groups.

1/1000 of the complex purified according to Example 2 (=10 nmol paclitaxel) was dissolved in 250 ml of DMEM culture medium (final concentration 40 nM). A similar charge was prepared with non-encapsulated taxol. The charges were added to culture cells (OAT SCLC), and the number of rounded cells (=cells in inhibited mitosis) was counted every 3 hours. The complexed taxol showed no mitosis-inhibiting effect on the culture cells within 24 hours (FIG. 2).

Figure 3:
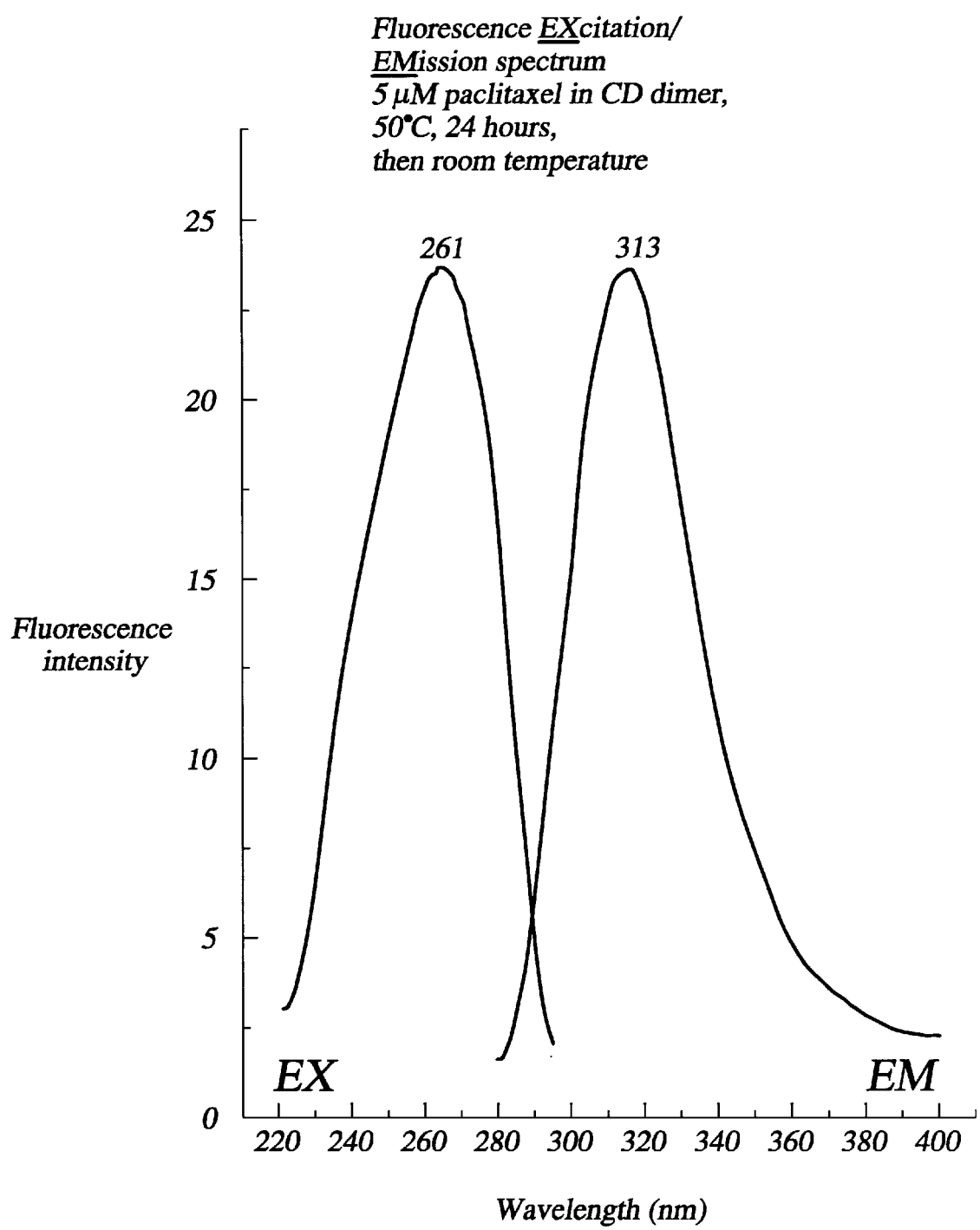
FIG. 3 shows the fluorescence spectrum of the batch according to Example 6. The encapsulated paclitaxel is monomerized.
Figure 4:
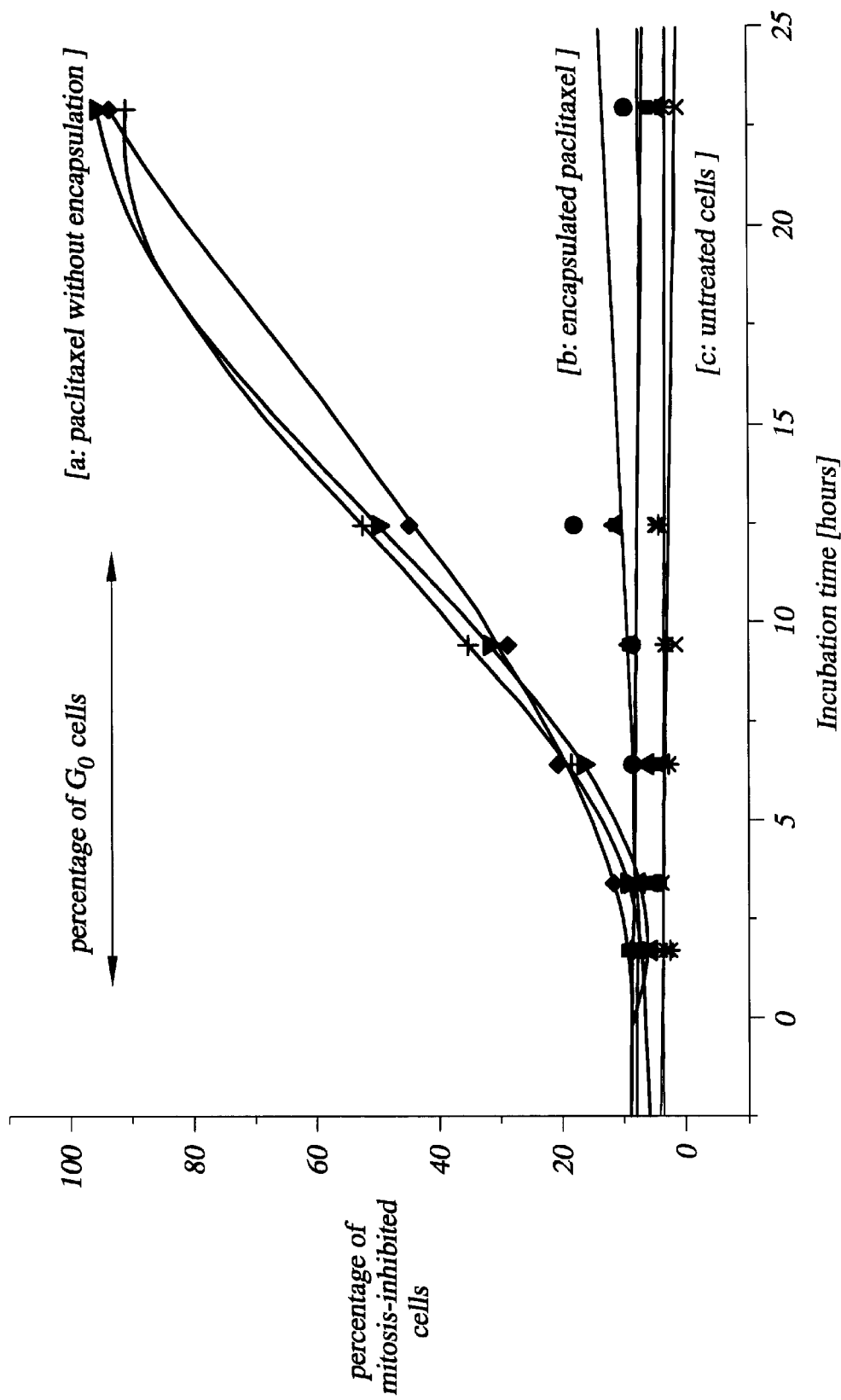
FIG. 4 shows the influence of free taxol and complexed taxol according to Example 8 on the mitosis of OAT cells. The upper three lines (crosses, triangles, diamonds) represent the effect of non-encapsulated taxol, the curves of squares, triangles and circles represent the effect of encapsulated taxol, and the three curves (crosses) represent untreated cells.

Treatment of the complex with the enzyme cyclodextrinase (from *Klebsiella oxytoca*) showed the release and reactivation of the complexed taxol from the complex in a similar experimental set-up (FIG. 3).

EXAMPLE 9

Specific Targeting of the Taxol Complex for Tumors of Mice

Xenografted OAT SCLC cells on nude mice were allowed to grow for 1 week for tumor formation. Thereafter, the mice were pretreated with the biotinylated monoclonal antibody ICO 25 for 24 hours by intraperitoneal injection of 1 mg of antibody per mouse. Then, 5 mg of NeutrAvidin were injected intraperitoneally. After an additional 48 hours, the complex formed from biotinylated (BiotinCadaverin)-CD dimer and paclitaxel (1–2–5 mg/mouse) was injected, and the growth of the tumor was followed over 4 weeks. The treated tumors grow at a maximum rate of 15% of the growth rate of untreated tumors (1–2 mg/mouse) or are completely eliminated (5 mg/mouse). Side-effects occurring with non-encapsulated taxol are not observed.

What is claimed is:

1. A cyclodextrin oligomer having the general formula

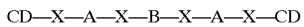

wherein X—A—B—X—A—X is a bifunctional spacer in which:

each X is selected from the group consisting of —NH—, —O—, —S—, —C(=O)— and a covalent bond;

each A is selected from the group consisting of a $C_2$ to $C_4$ alkylidenyl residues and a covalent bond;

B is selected from the group consisting of diradical linkers derived from melamine, 1,3,5-benzenetricarboxylic acid (aka trimesic acid), a tetracarboxylic acid derivative of 1,2-dihydroxyanthraquinone, a tetraamino derivative of 1,2-anthraquinone, α-cyclodextrin, β-cyclodextrin and γ-cyclodextrin; wherein each said cyclodextrin is bound through two primary carbons; and each terminal CD is bound through a secondary carbon; and wherein said cyclodextrin oligomer is optionally substituted with at least one affinity group which interacts with a molecular target structure.

2. The cyclodextrin oligomer according to claim 1, selected from the group consisting of:

1,3-{2°[β-CD]—N(H)—C(=O)}-5-carboxybenzene;

1,3-{2°[β-CD]—N(H)—$C_2H_4$—N(H)—C(=O)}-5-carboxybenzene;

β-CD—NH—($C_2H_4$)—S-(α-cyclodextrin)-S—($C_2H_4$)—NH-β-CD;

β-CD—NH—($C_2H_4$)—S-(β-cyclodextrin)-S—($C_2H_4$)—NH-β-CD;

β-CD—NH—($C_2H_4$)—S-(γ-cyclodextrin)-S—($C_2H_4$)—NH-β-CD; and 1,3-{2°[β-CD]—N(H)—$C_3H_6$—N(H)—C(=O)}-5-carboxybenzene.

3. The cyclodextrin oligomer according to claim 1, wherein said at least one affinity group is covalently bound to B of said spacer.

4. The cyclodextrin oligomer according to claim 1, wherein said at least one affinity group is a biotinyl residue or a digoxin/digoxigenin residue.

5. A physical inclusion complex consisting of a cyclodextrin oligomer according to claim 1 and a pharmaceutically active substance having restricted usage because of its high potential for undesirable side-effects.

6. The physical inclusion complex according to claim 5, wherein said pharmaceutically active substance is selected from the group consisting of mitotic inhibitors, tumor therapeutics and photochemotherapeutics.

7. The physical inclusion complex according to claim 5, wherein said pharmaceutically active substance is selected from the group consisting of taxol, a taxol derivative, colchicine, colchemide, $3^1,8^1$-(di-t-butylphenoxy)

porphyrin, phenytoin, chlorotrianisene, tamoxifene, vinblastine, vincristin and docetaxel.

8. A method for the preparation of the physical inclusion complexes of claim 5 comprising the steps of:
dissolving at least one pharmaceutically active substance in a first solvent to form a first solution;
dissolving a cyclodextrin oligomer according to claim 1 in a second solvent to form a second solution;
combining said first and second solutions to form a combined solution; and
heating said combined solution to evaporate said first solvent to enclose said pharmaceutically active substance within a physical inclusion complex of said cyclodextrin oligomer.

9. A method for the preparation of the cyclodextrin oligomers according to claim 1, comprising the steps of:
functionalizing cyclodextrins on their secondary sides by activation of OH groups on said cyclodextrins; and
reacting said OH groups with short bifunctional spacer groups.

10. A pharmaceutical composition comprising a physical inclusion complex according to claim 5 together with a pharmaceutically acceptable carrier.

11. A method of minimizing the side effects in the treatment of tumor diseases selected from the group consisting of tumors of the bladder, carcinomas of the breast or uterus, esophageal cancers, gasteric carcinomas, cephalo-cervical carcinomas, nasopharynx carcinoma, hepatocellular carcinomas, pulmonary carcinomas, lymphomas, melanomas, ovarial carcinomas and prostatic carcinomas comprising the steps of;
administering to a patient at least one pharmaceutically active substance selected from the group consisting of known anti-neoplastic agents active against the listed disease conditions in the form of a cyclodextrin oligomer complex wherein said cyclodextrin oligomer is defined by claim 1.

12. The cyclodextrin oligomer according to claim 1, where two of said affinity groups are attached to said cyclodextrin oligomer.

* * * * *